US009498300B1

(12) United States Patent
Sanchez, Jr.

(10) Patent No.: US 9,498,300 B1
(45) Date of Patent: Nov. 22, 2016

(54) COMMUNICATION SYSTEM FOR SURGICAL DEVICES

(71) Applicant: Novartis AG, Basel (CH)

(72) Inventor: Robert Joseph Sanchez, Jr., Oceanside, CA (US)

(73) Assignee: Novartis AG, Basel (CH)

( * ) Notice: Subject to any disclaimer, the term of this patent is extended or adjusted under 35 U.S.C. 154(b) by 3 days.

(21) Appl. No.: 14/813,509

(22) Filed: Jul. 30, 2015

(51) Int. Cl.
*H04B 10/00* (2013.01)
*A61F 9/007* (2006.01)

(52) U.S. Cl.
CPC ............ *A61B 90/92* (2016.02); *A61B 90/98* (2016.02); *A61F 9/00745* (2013.01); *A61B 2090/0805* (2016.02); *A61B 2090/309* (2016.02); *A61B 2217/005* (2013.01); *A61B 2560/0475* (2013.01)

(58) Field of Classification Search
USPC .................... 398/140, 106, 109, 141, 171
See application file for complete search history.

(56) References Cited

U.S. PATENT DOCUMENTS

| | | | | |
|---|---|---|---|---|
| 4,583,539 A * | 4/1986 | Karlin | ............... | A61B 18/20 219/121.74 |
| 4,614,437 A | 9/1986 | Buehler | | |
| 4,796,641 A * | 1/1989 | Mills | ............... | A61B 5/0215 128/903 |
| 4,803,992 A * | 2/1989 | Lemelson | ......... | A61B 1/00096 600/342 |
| 4,815,471 A * | 3/1989 | Stobie | ............... | A61B 5/0215 600/348 |
| 5,065,010 A * | 11/1991 | Knute | ............... | A61B 5/02154 250/205 |
| 5,200,604 A * | 4/1993 | Rudko | ............... | A61B 18/20 219/121.62 |
| 5,247,171 A * | 9/1993 | Wlodarczyk | ...... | A61B 5/02154 250/227.21 |
| 5,437,284 A * | 8/1995 | Trimble | ............... | A61B 5/031 600/486 |
| 5,531,698 A * | 7/1996 | Olsen | ............... | A61M 5/142 128/DIG. 12 |
| 5,579,774 A * | 12/1996 | Miller | ............... | A61B 5/031 600/479 |
| 5,617,857 A * | 4/1997 | Chader | ............... | A61B 5/06 128/899 |
| 5,651,780 A * | 7/1997 | Jackson | ............... | A61B 18/00 606/1 |
| 5,738,677 A * | 4/1998 | Colvard | ............... | A61F 9/00802 128/898 |
| 5,957,912 A * | 9/1999 | Heitzmann | ....... | A61M 25/0029 600/561 |
| 6,017,354 A * | 1/2000 | Culp | ............... | A61B 90/98 604/22 |
| 6,210,346 B1 * | 4/2001 | Hall | ............... | A61B 5/031 600/561 |
| 6,266,551 B1 * | 7/2001 | Osadchy | ............... | A61B 34/20 600/424 |
| 6,370,411 B1 * | 4/2002 | Osadchy | ............... | A61B 5/06 600/372 |
| 6,437,316 B1 * | 8/2002 | Colman | ............... | A61M 39/10 250/222.1 |
| 6,595,930 B2 * | 7/2003 | Rosenheimer | ......... | A61B 5/031 600/300 |
| 6,623,423 B2 * | 9/2003 | Sakurai | ............... | A61B 17/32006 600/104 |
| 6,711,440 B2 * | 3/2004 | Deal | ............... | A61N 1/372 607/9 |
| 6,962,583 B2 * | 11/2005 | Kadziauskas | .. | A61B 17/320068 604/22 |
| 6,980,848 B2 * | 12/2005 | Helfer | ............... | A61B 5/055 600/423 |
| 7,383,073 B1 * | 6/2008 | Abovitz | ............... | G06F 8/67 600/407 |
| 7,389,137 B2 * | 6/2008 | Helfer | ............... | A61B 5/055 324/318 |
| 7,450,996 B2 * | 11/2008 | MacDonald | ........... | A61N 1/056 607/115 |
| 7,575,381 B2 * | 8/2009 | Boutoussov | ........... | A61B 18/22 385/88 |
| 7,780,652 B2 * | 8/2010 | MacFarland | ......... | A61B 18/203 606/1 |

(Continued)

*Primary Examiner* — Agustin Bello
(74) *Attorney, Agent, or Firm* — Kenneth D. Bassinger

(57) ABSTRACT

A communication system includes an instrument connector with a light source and a connector antenna; and a console connector with a photo sensor and a console antenna. The light source is configured to produce light that is received by the photo sensor when the instrument connector is coupled to the console connector. The light source may also be configured to produce a series of light pulses, the series of light pulses identifying the surgical instrument coupled to the instrument connector. The light source may also be configured to produce light of a particular color, the color of the light identifying the surgical instrument coupled to the instrument connector. The light source may also be configured to produce a series of light pulses of a particular color, the series of light pulses and the color of the light identifying the surgical instrument coupled to the instrument connector.

17 Claims, 6 Drawing Sheets

(56) References Cited

U.S. PATENT DOCUMENTS

| | | | |
|---|---|---|---|
| 7,873,400 B2* | 1/2011 | Moctezuma De La Barrera | A61B 90/36 382/103 |
| 8,066,681 B1* | 11/2011 | Hall | A61B 5/031 600/561 |
| 8,357,148 B2* | 1/2013 | Boulais | A61B 1/00059 606/34 |
| 8,358,883 B2* | 1/2013 | Prisco | G01L 1/246 385/12 |
| 8,360,968 B2* | 1/2013 | Hadani | A61B 1/00105 600/121 |
| 8,537,203 B2* | 9/2013 | Seibel | A61B 1/0008 348/45 |
| 8,561,473 B2* | 10/2013 | Blumenkranz | A61B 19/2203 385/13 |
| 8,622,935 B1* | 1/2014 | Leo | A61B 5/6843 600/585 |
| 8,663,204 B2* | 3/2014 | Lechner | A61B 34/74 606/1 |
| 8,708,929 B2* | 4/2014 | Videbaek | A61B 10/0275 210/232 |
| 8,708,930 B2* | 4/2014 | Videbaek | A61B 10/0275 210/232 |
| 8,749,396 B2* | 6/2014 | Maggiore | G06T 19/006 340/540 |
| 8,761,865 B2* | 6/2014 | Babchenko | A61B 5/0075 600/473 |
| 8,814,855 B2* | 8/2014 | DiCarlo | A61B 18/1206 606/34 |
| 8,961,436 B2* | 2/2015 | Leo | A61B 5/0084 600/587 |
| 9,135,669 B2* | 9/2015 | Roemerman | G06Q 10/08 |
| 9,173,641 B2* | 11/2015 | Chudzik | A61B 10/0275 |
| 9,282,949 B2* | 3/2016 | Videbaek | A61B 10/0275 |
| 9,283,334 B2* | 3/2016 | Mantell | A61M 13/00 |
| 9,301,687 B2* | 4/2016 | Kemp | A61B 5/6852 |
| 9,345,458 B2* | 5/2016 | Videbaek | A61B 10/0275 |
| 9,383,263 B2* | 7/2016 | Welford | A61B 5/0066 |
| 2001/0034530 A1* | 10/2001 | Malackowski | A61B 34/20 606/130 |
| 2002/0016599 A1* | 2/2002 | Kienzle, III | A61B 17/1703 606/130 |
| 2002/0111608 A1* | 8/2002 | Baerveldt | A61F 9/00781 606/6 |
| 2003/0055413 A1* | 3/2003 | Altshuler | A61B 18/203 606/9 |
| 2005/0020909 A1* | 1/2005 | Moctezuma de la Barrera | A61B 34/20 600/424 |
| 2005/0131426 A1* | 6/2005 | Moctezuma de la Barrera | A61B 90/36 606/130 |
| 2005/0137655 A1* | 6/2005 | MacFarland | A61B 18/203 607/88 |
| 2006/0142740 A1* | 6/2006 | Sherman | A61B 1/0005 606/1 |
| 2006/0189858 A1* | 8/2006 | Sterling | A61B 5/14532 600/310 |
| 2007/0078328 A1* | 4/2007 | Ozaki | A61B 1/00059 600/407 |
| 2007/0213590 A1* | 9/2007 | Squicciarini | A61B 1/00087 600/172 |
| 2007/0274626 A1* | 11/2007 | Sabeta | A45C 11/005 385/24 |
| 2008/0021274 A1* | 1/2008 | Bayer | A61B 1/0008 600/112 |
| 2009/0036846 A1* | 2/2009 | Dacquay | A61F 9/0017 604/290 |
| 2009/0069714 A1* | 3/2009 | Eichmann | A61B 5/002 600/573 |
| 2009/0123111 A1* | 5/2009 | Udd | A61B 5/06 385/13 |
| 2009/0294521 A1* | 12/2009 | de la Huerga | A61J 1/035 235/375 |
| 2010/0168711 A1 | 7/2010 | Bazargan et al. | |
| 2010/0174415 A1* | 7/2010 | Humayun | A61B 19/0271 700/282 |
| 2010/0262002 A1* | 10/2010 | Martz | A61M 5/14566 600/432 |
| 2010/0272442 A1* | 10/2010 | Lechner | A61B 34/74 398/106 |
| 2011/0190690 A1* | 8/2011 | Humayun | A61B 90/98 604/22 |
| 2011/0202069 A1* | 8/2011 | Prisco | G01D 5/35316 606/130 |
| 2011/0224825 A1* | 9/2011 | Larkin | A61B 19/2203 700/254 |
| 2011/0264069 A1 | 10/2011 | Bochenko | |
| 2011/0280374 A1* | 11/2011 | Ohta | G01T 1/243 378/114 |
| 2012/0123392 A1* | 5/2012 | McKinnon | A61M 39/10 604/533 |
| 2012/0136383 A1* | 5/2012 | Boutoussov | A61C 1/0046 606/190 |
| 2012/0265102 A1* | 10/2012 | Leo | A61B 5/6852 600/587 |
| 2012/0277531 A1* | 11/2012 | Krattiger | G01B 7/18 600/117 |
| 2012/0330684 A1 | 12/2012 | Jacobs et al. | |
| 2013/0225945 A1* | 8/2013 | Prince | G06F 19/3456 600/301 |
| 2013/0267894 A1* | 10/2013 | Woolford | A61B 1/317 604/67 |
| 2013/0273494 A1* | 10/2013 | Boutoussov | A61C 1/0046 433/29 |
| 2013/0345719 A1* | 12/2013 | Donhowe | A61B 1/00167 606/130 |
| 2014/0021251 A1* | 1/2014 | Colman | B01L 3/565 235/375 |
| 2014/0052114 A1* | 2/2014 | Ben-Oren | A61B 17/320016 606/15 |
| 2014/0323813 A1* | 10/2014 | Humayun | A61B 90/98 600/249 |
| 2014/0365235 A1* | 12/2014 | DeBoer | A61B 34/10 705/2 |
| 2015/0018622 A1* | 1/2015 | Tesar | A61B 1/05 600/202 |
| 2015/0025446 A1* | 1/2015 | Jacobson | A61F 9/00736 604/22 |
| 2015/0282985 A1* | 10/2015 | Ross | A61M 1/0058 604/30 |
| 2015/0335797 A1* | 11/2015 | Muri | A61M 1/0058 604/35 |
| 2016/0100908 A1* | 4/2016 | Tesar | A61B 17/02 600/202 |
| 2016/0103810 A1* | 4/2016 | Hanning | G06F 3/167 715/226 |
| 2016/0151557 A1* | 6/2016 | Woolford | A61B 1/00039 606/86 R |

* cited by examiner

COMMUNICATION SYSTEM FOR SURGICAL DEVICES

BACKGROUND OF THE INVENTION

The present invention relates to a system for identifying devices used during surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigation sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigation sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is introduced into the eye, passing between the irrigation sleeve and the cutting needle and exiting into the eye at the tip of the irrigation sleeve and/or from one or more ports, or openings, in the irrigation sleeve near its end. The irrigating fluid protects the eye tissues from the heat generated by the vibrating of the ultrasonic cutting needle. Furthermore, the irrigating fluid suspends the fragments of the emulsified lens for aspiration from the eye.

A wide range of devices are used during a typical phacoemulsification procedure—for example, fluidics cassettes, needles, cannulas, irrigation tips, aspiration tips, hand pieces, and other devices. In other ophthalmic surgical procedures, various probes, scissors, cutters, illuminators, laser probes, and the like are used. In each case, these devices are operably attached to a surgical console and must be identified by the console to ensure proper operation. Prior methods of identification include using bar codes or radio frequency identification (RFID) systems. Bar codes require a separate scanner, and RFID systems are susceptible to interference. It would be desirable to have an automatic way of detecting the differences among these devices or probes used during a procedure.

SUMMARY OF THE INVENTION

In one embodiment consistent with the principles of the present invention, the present invention is a communication system with an instrument connector comprising a light source and a connector antenna; and a console connector comprising a photo sensor and a console antenna. The light source is configured to produce light that is received by the photo sensor when the instrument connector is coupled to the console connector. The light source may also be configured to produce a series of light pulses, the series of light pulses identifying a surgical instrument coupled to the instrument connector. The light source may also be configured to produce light of a particular color, the color of the light identifying a surgical instrument coupled to the instrument connector. The light source may also be configured to produce a series of light pulses of a particular color, the series of light pulses and the color of the light identifying a surgical instrument coupled to the instrument connector. The console antenna and the connector antenna may be inductively coupled so that the console connector provides power to the instrument connector. The instrument connector may further comprise an alignment feature and the console connector further comprises a complementary alignment feature. The instrument connector may also comprise a connector photo sensor and the console connector may also comprise a console light source. In this case, the light source is configured to produce a first series of light pulses and the photo sensor is configured to receive the first series of light pulses, the first series of light pulses identifying a surgical instrument coupled to the instrument connector; and the console light source is configured to produce a second series of light pulses and the connector photo sensor is configured to receive the second series of light pulses, the second series of light pulses representing information about a console. The instrument connector may also comprise a face that permits the passage of light created by the light source, a memory, and circuitry for driving the light source. The light source may be a light emitting diode.

In another embodiment consistent with the principles of the present invention, the present invention is a communication system with a cassette comprising a light source and a cassette antenna; and a cassette receiver comprising a photo sensor and a fluidics antenna. The light source is configured to produce light that is received by the photo sensor when the cassette is coupled to the cassette receiver. The light source may also be configured to produce a series of light pulses, the series of light pulses identifying the cassette. The light source may also be configured to produce light of a particular color, the color of the light identifying the cassette. The light source may also be configured to produce a series of light pulses of a particular color, the series of light pulses and the color of the light identifying the cassette. The fluidics antenna and the cassette antenna may be inductively coupled so that the cassette receiver provides power to the cassette. The cassette may also comprise a cassette photo sensor and the cassette receiver may also comprise a receiver light source. In this case, the light source is configured to produce a first series of light pulses and the photo sensor is configured to receive the first series of light pulses, the first series of light pulses identifying a cassette; and the receiver light source is configured to produce a second series of light pulses and the cassette photo sensor is configured to receive the second series of light pulses, the second series of light pulses representing information about a console. The cassette may also comprise a face that permits the passage of light created by the light source, a memory, and circuitry for driving the light source. The light source may be a light emitting diode.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
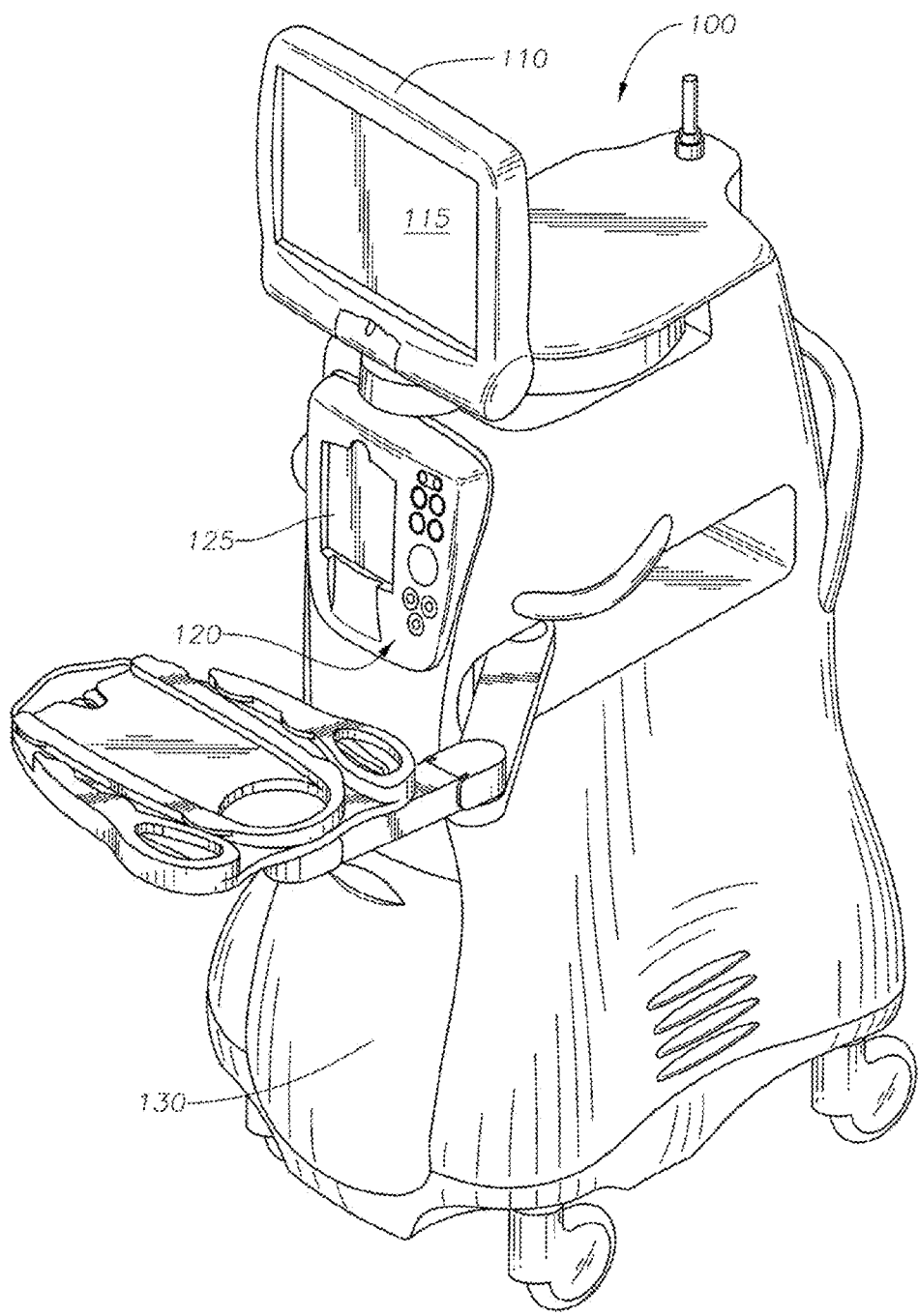
FIG. 1 is a schematic diagram of a surgical console.

FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a GUI that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features.

Connection panel 120 provides a variety of connections for surgical instruments, such as hand pieces, and consumables, such as fluidics cassettes. Surgical console 100 is designed to operate with a variety of surgical instruments and consumables. As such, surgical console 100 must identify or recognize a particular surgical instrument or consumable that is inserted into connection panel 120 in order to ensure safe and effective operation. When a variety of surgical instruments and consumables may be used with surgical console 100, specifically identifying the various types allows surgical console 100 to operate properly.

Figure 2:
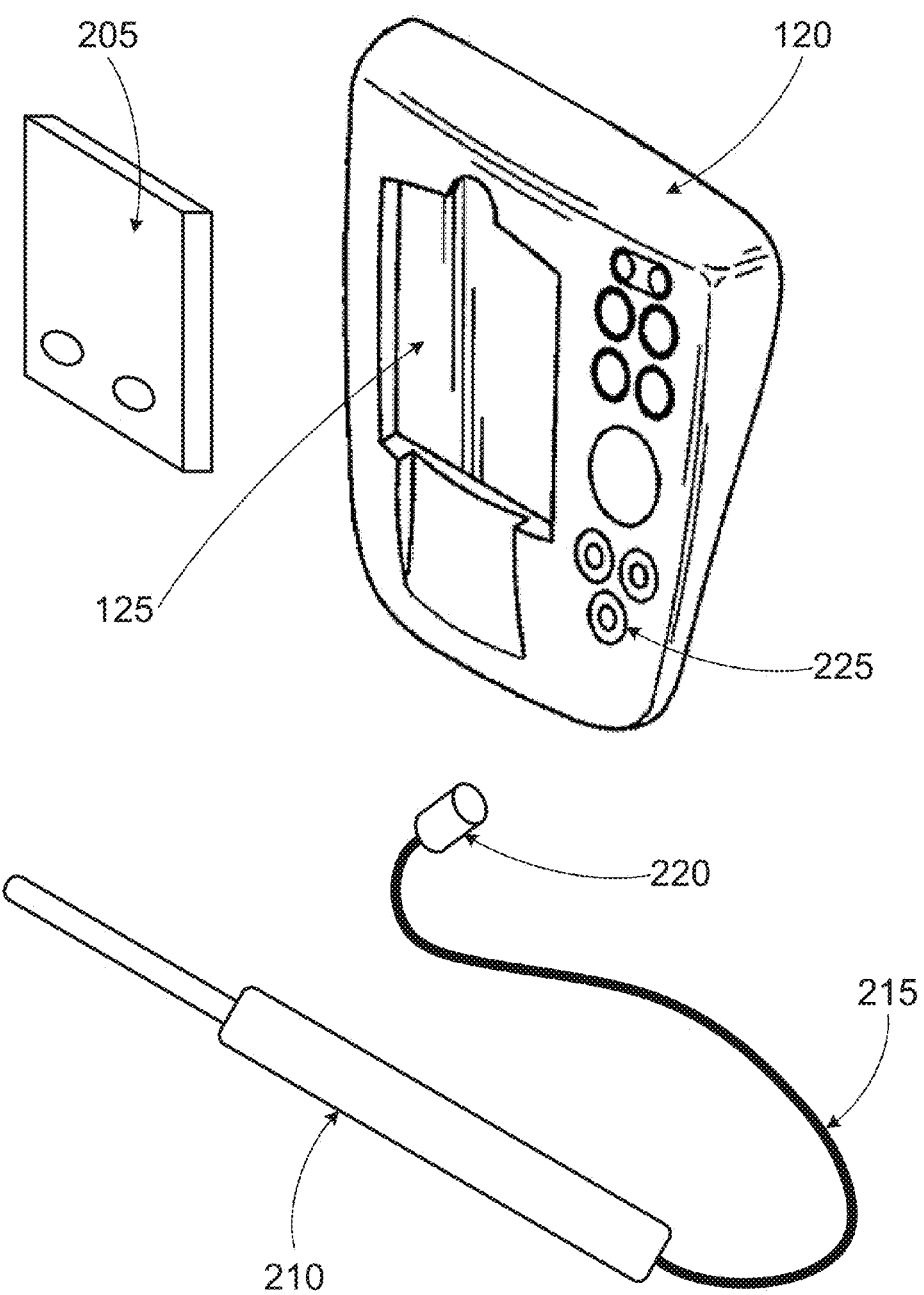
FIG. 2 is a perspective view of a connector or interface portion of a surgical console.

FIG. 2 is a perspective view of a connection panel 120, a fluidics cassette 205, and a surgical instrument 210. Connection panel 120 includes at least one console connector 225 and a cassette receiver 125. Cassette receiver 125 accepts fluidics cassette 205. Fluidics cassette 205 fits into cassette receiver 125 to provide a fluid path during a surgical procedure. For example, fluidics cassette 205 may provide a positive displacement pump, venturi pump capability, pressure sensors, valves, and other functions associated with a fluidics path. Surgical instrument 210 includes cable 215 and instrument connector 220. Instrument connector 220 interfaces with console connector 225. In this manner, instrument connector 220 operably couples surgical instrument 210 to console 100. For example, when surgical instrument is an ophthalmic instrument, cable 215 may provide power and communications functionality to surgical instrument 210. Cable 215 may also provide a fluidics path to surgical instrument 210. Instrument connector 220 plugs into console connector 225 in console 100. Instrument connector 220 also serves to identify the type of surgical instrument 210 as described below.

Figure 3:
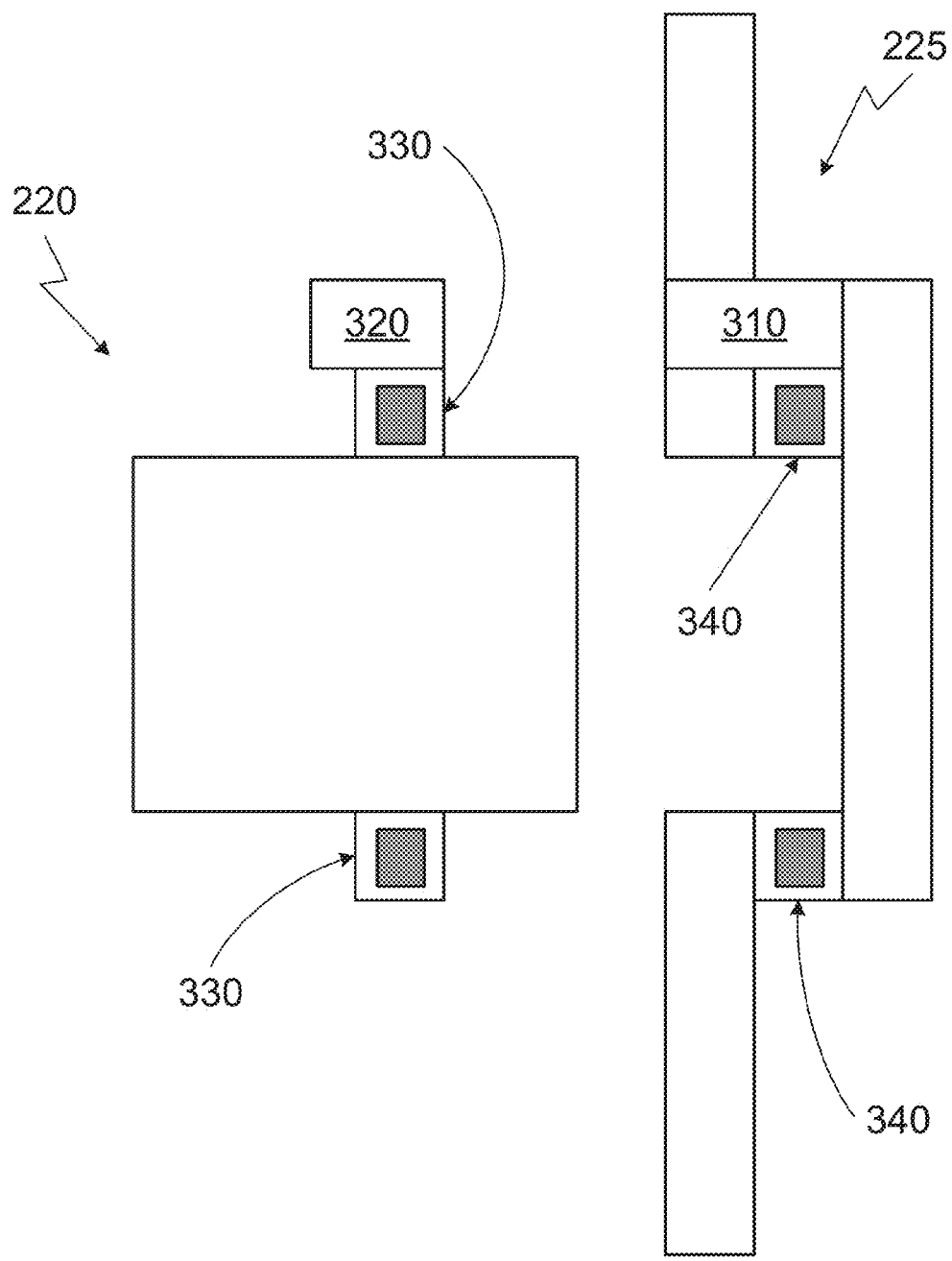
FIG. 3 is a cross section view of an identification system.

FIG. 3 is a cross section view of an identification system. FIG. 3 depicts a cross section of one embodiment of instrument connector 220 and console connector 225. In this example, instrument connector 220 comprises a light source 320 and a connector antenna 330. Light source 320 is integrated with instrument connector 220. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Connector antenna 330 provides an inductive connection with console antenna 340. Connector antenna 330 is disposed around the periphery of instrument connector 220.

In this example, console connector 225 includes a photo sensor 310 and console antenna 340. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Console antenna 340 provides an inductive connection with connector antenna 330. Console antenna 340 is disposed in console connector 225 so that it is aligned with connector antenna 330 when instrument connector 220 is received in console connector 225.

Figure 4:
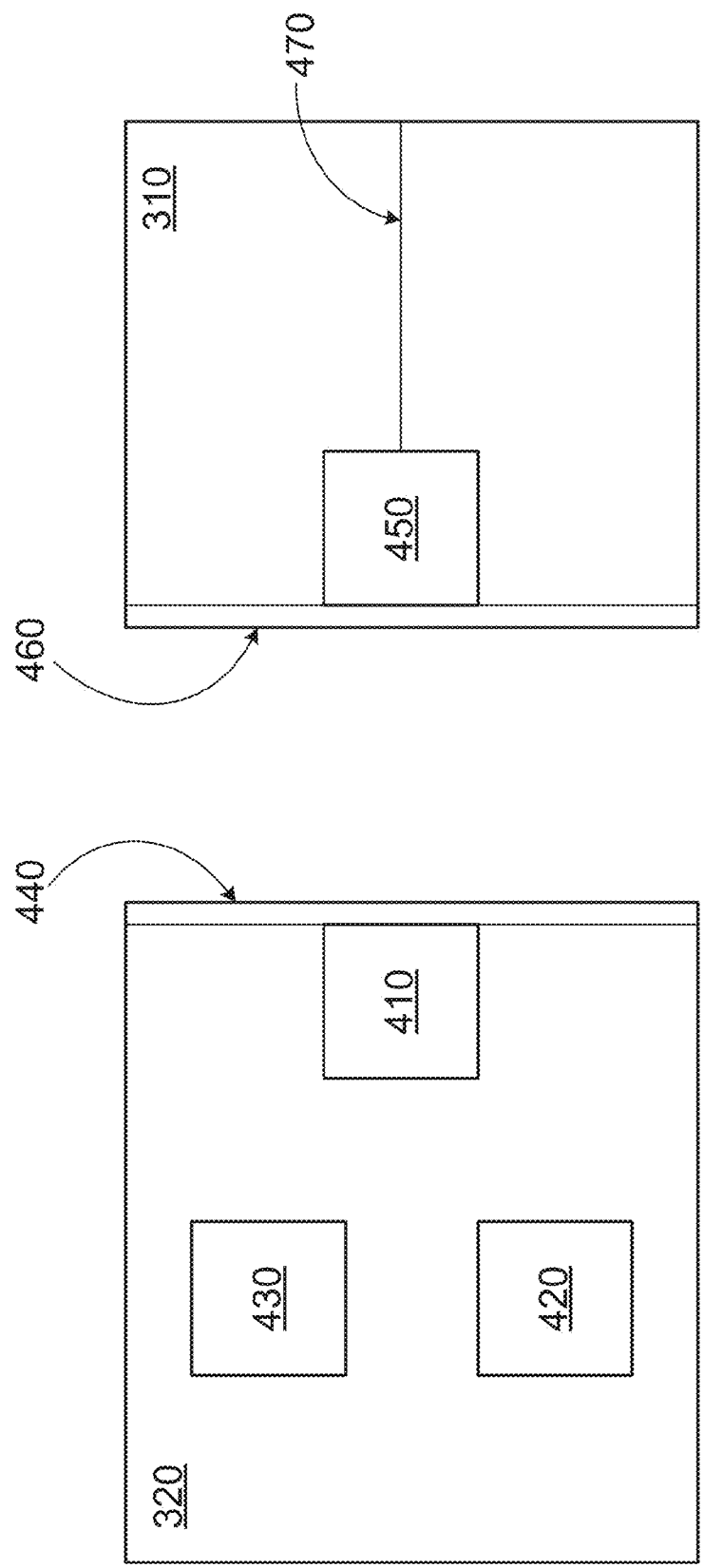
FIG. 4 is a cross section view of an identification system.

FIG. 4 is a cross section view of an identification system. In the example of FIG. 4, light source 320 includes one or more LED 410, memory 420, circuitry 430, and an instrument connector face 440. LED 410 may be of any color or number. For example, LED 410 may contain a single LED of any color or multiple LEDs of the same or different colors. In one example, LED 410 includes a single LED where the color of the LED provides an indication of the type of surgical instrument 210 or where a pulse pattern produced by the LED provides an indication of the type of surgical instrument 210. In another example, LED 410 includes LEDs of different colors where the color combination of different LEDs provides an indication of the type of surgical instrument 210, or a pulsed color pattern provides an indication of the type of surgical instrument 210. A memory 420 is provided to store information associated with an indication of the type of surgical instrument 210. Circuitry 430 is provided to drive LED 410. Circuitry 430 may be employed in addition to or in place of memory 440. Instrument connector face 440 is transparent or translucent so that light emitted from LED 410 can exit light source 320. In one example, instrument connector face 440 may be polarized or include a light altering element.

In the example of FIG. 4, photo sensor 310 includes a camera 450, console connector face 460, and wire 470. While photo sensor 310 is described as having a camera 450, any other type of device such as a photo detector, image sensor, radiation detector, optical detector, photo resistor, photovoltaic cell, photodiode, phototransistor or similar device may be employed in place of camera 450. Console connector face 460 is transparent or translucent so that light emitted from LED 410 can enter camera 450. In one example, console connector face 460 may be polarized or include a light altering element. Wire 470 connects camera 450 to circuitry in surgical console 100 such as memory, decoders, processors, controllers, or the like. In another example, this circuitry may also be included in photo sensor 310.

Figure 5:
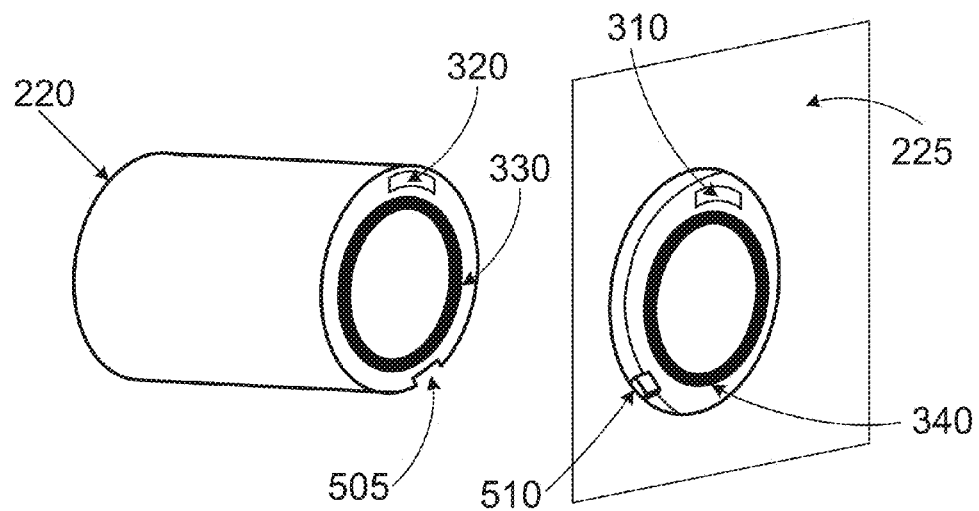
FIG. 5 is a perspective view of an identification system.

FIG. 5 is a perspective view of an identification system. In the example of FIG. 5, instrument connector comprises a light source 320, a connector antenna 330, and alignment notch 505. Light source 320 is integrated with instrument connector 220. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Light source 320 may also include an instrument connector face 440 to allow light to exit light source 320. An alignment notch 505 is provided to properly align instrument connector 220 in console connector 225. Connector antenna 330 provides an inductive connection with console antenna 340. Connector antenna 330 is disposed around the periphery of instrument connector 220.

In this example, console connector 225 includes a photo sensor 310, console antenna 340, and an alignment protrusion 510. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Console antenna 340 provides an inductive connection with connector antenna 330. Console antenna 340 is disposed in console connector 225 so that it is aligned with connector antenna 330 when instrument connector 220 is received in console connector 225. In some cases, alignment protrusion 510 is also provided to properly align instrument connector 220 in console connector 225.

Figure 6:
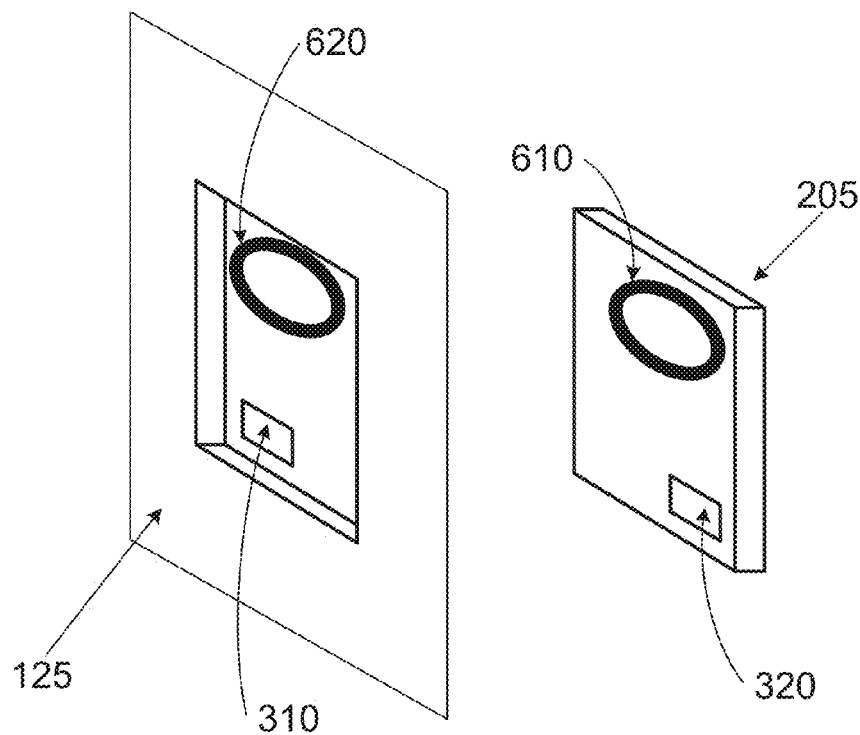
FIG. 6 is a perspective view of an identification system.

FIG. 6 is a perspective view of an identification system. In the example of FIG. 6, cassette 205 comprises a light source 320, and a cassette antenna 610. Light source 320 is integrated with cassette 205. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Light source 320 may also include an instrument connector face 440 to allow light to exit light source 320. Cassette antenna 610 provides an inductive connection with fluidics antenna 620.

In this example, cassette receiver 125 includes a photo sensor 310 and fluidics antenna 620. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Fluidics antenna 620 provides an inductive connection with cassette antenna 610. Cassette antenna 610 is disposed in cassette 205 so that it is aligned with fluidics antenna 620 when cassette 205 is received in cassette receiver 125.

The principles of the examples of FIGS. 3, 4, and 5 may also be employed with the system of FIG. 6. For example, light source 320 located in cassette 205 may also include a transparent or translucent face like instrument connector face 440. Likewise, photo sensor 310 in cassette receiver 125 may also include a transparent or translucent face like console connector face 460.

In operation, the examples of FIGS. 2-6 provide a system to identify the surgical instrument 210 or cassette 205 that is coupled to surgical console 100. For example, light source 320 may contain a single white LED that is programmed to provide a series of pulses. The number and/or duration of the pulses in the series of pulses can be used to identify the particular surgical instrument 210 or cassette 205 that is coupled to surgical console 100. For example, a series of three short pulses may identify a particular surgical instrument, while a series of five short pulses may identify a different surgical instrument. A code, such as Morse code, may be employed to communicate data identifying the surgical instrument 210 or cassette 205 that is coupled to surgical console 100.

In another example, light source 320 may contain a single LED of a certain color. The color of the LED can be used to identify the particular surgical instrument 210 or cassette 205 that is coupled to surgical console 100. In this manner, different devices may include LEDs of different colors. For example, a red LED may identify a particular surgical instrument or cassette, while a blue LED may identify a different surgical instrument or cassette. In another example, the LED may also be pulsed as previously described. For example, a red LED may be pulsed in a sequence to identify a particular instrument or cassette while a blue LED may be pulsed in the same or different sequence to identify a different surgical instrument or cassette. In this manner, the color of the LED may identify a class of instruments or cassettes while a particular pulse sequence may identify the particular instrument or cassette in that class.

In another example, light source 320 may contain multiple LEDs of different colors. The LEDs can be illuminated together to produce a color that can be used to identify the particular surgical instrument 210 or cassette 205 that is coupled to surgical console 100. Alternatively, the LEDs can be pulsed in a sequence so that a sequence of colors can be used to identify the particular surgical instrument 210 or cassette 205 that is coupled to surgical console 100.

Regardless of the type of light or pulsed light communication used, console antenna 340 inductively couples with connector antenna 330 when instrument connector 220 is inserted in console connector 225. In one example, console 100 provides power to instrument connector 320 through this inductive link. Likewise, cassette antenna 610 inductively couples with fluidics antenna 620 when cassette 205 is inserted into cassette receiver 125. In one example, console 100 provides power to cassette 205 through this inductive link.

Figure 7:
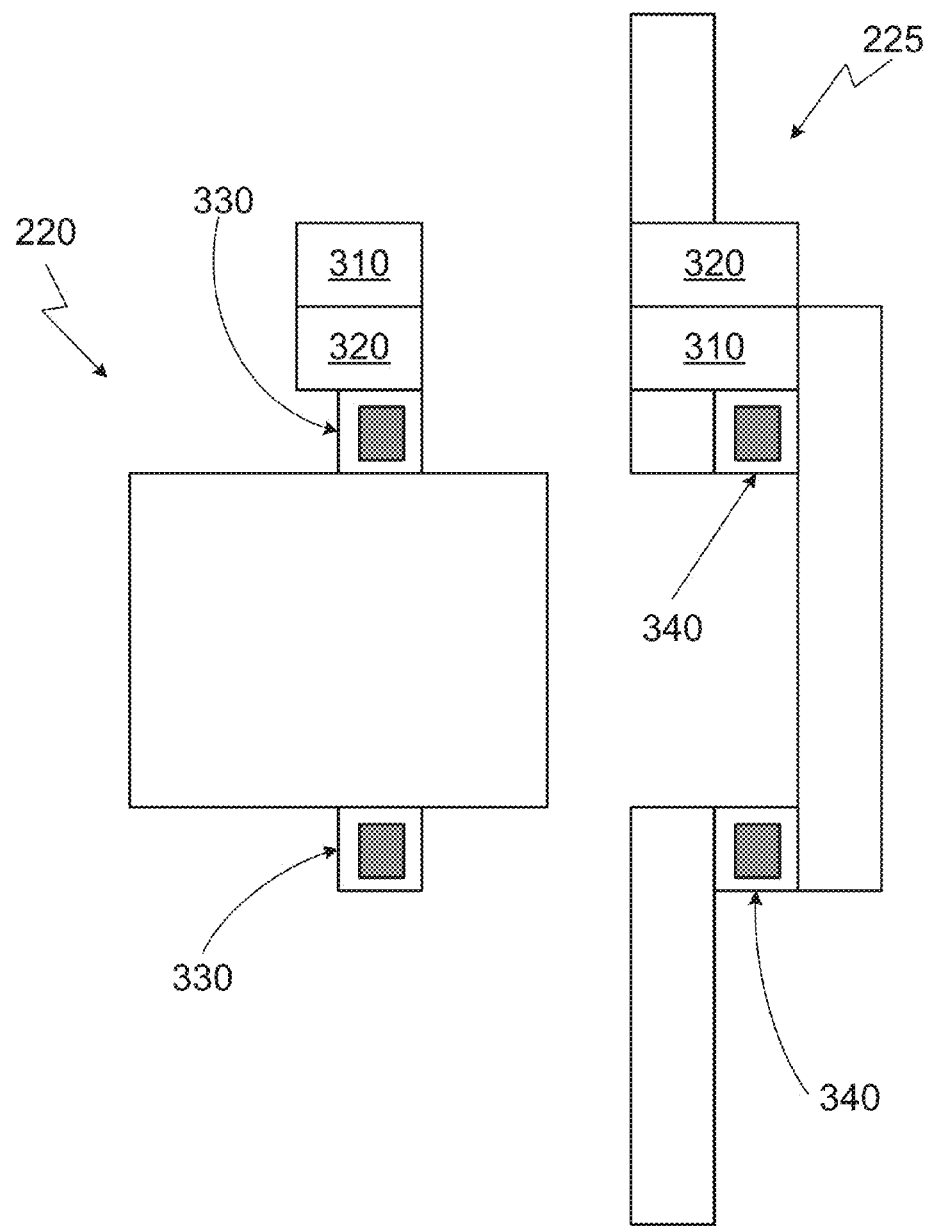
FIG. 7 is a cross section view of an identification system.

FIG. 7 is a cross section view of an identification system. FIG. 7 depicts a cross section of one embodiment of instrument connector 220 and console connector 225 that allows for two-way communication. In this example, instrument connector 220 comprises a light source 320, a photo sensor 310, and a connector antenna 330. Light source 320 and photo sensor 310 are integrated with instrument connector 220. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Connector antenna 330 provides an inductive connection with console antenna 340. Connector antenna 330 is disposed around the periphery of instrument connector 220.

In this example, console connector 225 comprises a light source 320, a photo sensor 310, and a console antenna 340. Light source 320 and photo sensor 310 are integrated with console connector 225. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Connector antenna 330 provides an inductive connection with console antenna 340. Console antenna 340 is disposed around the periphery of console connector 225 so as to allow for proper alignment between connector antenna 330 and console antenna 340. This alignment enables inductive coupling between connector antenna 330 and console antenna 340.

While FIG. 7 is described in terms of an instrument connector 220 and a console connector 225, the same principles may be applied to a cassette 205 and cassette receiver 125. For example, cassette 205 may comprise a light source 320, a photo sensor 310, and a cassette antenna 610. In such as case, light source 320 and photo sensor 310 are integrated with cassette 205. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Cassette antenna 610 provides an inductive connection with fluidics antenna 620. Cassette antenna 610 is disposed in cassette 205 so as to allow for proper alignment between cassette antenna 610 and fluidics antenna 620. This alignment enables inductive coupling between cassette antenna 610 and fluidics antenna 620.

In this example, cassette receiver 125 may comprise a light source 320, a photo sensor 310, and a fluidics antenna 620. In such as case, light source 320 and photo sensor 310 are integrated with cassette 205. Light source 320 may include any type of light source such as a lamp, phosphorescent device, or light emitting diode (LED). When light source 320 includes an LED, any number and type of LED may be used. For example, light source 320 may employ a red, blue, white or any other color of LED. Light source may employ any number of LEDs as well. Light source 320 typically includes circuitry for driving the LED. For example, light source 320 may include a small printed circuit board (PCB), a small memory chip, and circuitry for driving one or more LEDs. Photo sensor 310 may be a camera (e.g. CCD or CMOS), photo detector, image sensor, radiation detector, optical detector, photo resistor, photovoltaic cell, photodiode, phototransistor or similar device. In this example photo sensor 310 is housed in a transparent or translucent housing to allow light emitted from light source 320 to reach photo sensor 310. Photo sensor 310 may also include a PCB, decoder, memory, driving circuitry, or other circuitry used to operate photo sensor 310. Fluidics antenna 620 provides an inductive connection with cassette antenna 610. Fluidics antenna 620 is disposed in cassette receiver 125 so as to allow for proper alignment between cassette antenna 610 and fluidics antenna 620. This alignment enables inductive coupling between cassette antenna 610 and fluidics antenna 620.

In operation, the system of FIG. 7 allows for two-way communication between instrument connector 220 and console connector 225 or between cassette 205 and cassette receiver 125. Any of the above described methods of communicating using light pulses, colored light or a combination thereof may be employed for two-way communication. For simplicity, this operation is described with respect to instrument connector 220 and console connector 225, but the same principles apply equally to cassette 205 and cassette receiver 125. In one example, instrument connector 220 communicates with console connector 225 to identify the type of surgical instrument. Console connector 225 communicates with instrument connector to identify properties associated with console 100. For example, console connector 225 may communicate parameters measured by console 100, features of console 100, particular software revisions or capabilities residing in console 100 or any other information that may be used to calibrate or operate the surgical instrument. In another example, calibration information is exchanged between console 100 and surgical instrument 210. In another example, a series of light pulses represents information about the surgical console 100.

From the above, it may be appreciated that the present invention provides an improved system for identifying device connected to a surgical console. The present invention provides a device with light-emitting capability and a surgical console with complementary light detecting capability. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A communication system comprising:
   an instrument connector comprising:
      a light source; and
      a connector antenna; and
   a console connector comprising:
      a photo sensor; and
      a console antenna
   wherein the light source is configured to produce light that is received by the photo sensor when the instrument connector is coupled to the console connector.

2. The communication system of claim 1 wherein the light source is configured to produce a series of light pulses, the series of light pulses identifying a surgical instrument coupled to the instrument connector.

3. The communication system of claim 1 wherein the light source is configured to produce light of a particular color, the color of the light identifying a surgical instrument coupled to the instrument connector.

4. The communication system of claim 1 wherein the light source is configured to produce a series of light pulses of a particular color, the series of light pulses and the color of the light identifying a surgical instrument coupled to the instrument connector.

5. The communication system of claim 1 wherein the console antenna and the connector antenna are inductively coupled so that the console connector provides power to the instrument connector.

6. The communication system of claim 1 wherein the instrument connector further comprises an alignment feature and the console connector further comprises a complementary alignment feature.

7. The communication system of claim 1 wherein the instrument connector further comprises a connector photo sensor and the console connector further comprises a console light source.

8. The communication system of claim 7 wherein:
   the light source is configured to produce a first series of light pulses and the photo sensor is configured to receive the first series of light pulses, the first series of light pulses identifying a surgical instrument coupled to the instrument connector; and
   the console light source is configured to produce a second series of light pulses and the connector photo sensor is configured to receive the second series of light pulses, the second series of light pulses representing information about a console.

9. The communication system of claim 1 wherein the instrument connector further comprises:
   a face that permits the passage of light created by the light source,
   a memory, and
   circuitry for driving the light source,
   and further wherein the light source is a light emitting diode.

10. A communication system comprising:
   a cassette comprising:
      a light source; and
      a cassette antenna; and
   a cassette receiver comprising:
      a photo sensor; and
      a fluidics antenna
   wherein the light source is configured to produce light that is received by the photo sensor when the cassette is coupled to the cassette receiver.

11. The communication system of claim 10 wherein the light source is configured to produce a series of light pulses, the series of light pulses identifying the cassette.

12. The communication system of claim 10 wherein the light source is configured to produce light of a particular color, the color of the light identifying the cassette.

13. The communication system of claim 10 wherein the light source is configured to produce a series of light pulses of a particular color, the series of light pulses and the color of the light identifying the cassette.

14. The communication system of claim 10 wherein the fluidics antenna and the cassette antenna are inductively coupled so that the cassette receiver provides power to the cassette.

15. The communication system of claim 10 wherein the cassette further comprises a cassette photo sensor and the cassette receiver further comprises a receiver light source.

16. The communication system of claim 15 wherein:
the light source is configured to produce a first series of light pulses and the photo sensor is configured to receive the first series of light pulses, the first series of light pulses identifying a cassette; and
the receiver light source is configured to produce a second series of light pulses and the cassette photo sensor is configured to receive the second series of light pulses, the second series of light pulses representing information about a console.

17. The communication system of claim 10 wherein the cassette further comprises:
a face that permits the passage of light created by the light source,
a memory, and
circuitry for driving the light source,
and further wherein the light source is a light emitting diode.

* * * * *